United States Patent [19]
Fergason et al.

[11] Patent Number: 5,515,186
[45] Date of Patent: May 7, 1996

[54] EYE PROTECTION DEVICE FOR WELDING HELMETS WHICH REDUCES OBLIQUELY INCIDENT LIGHT

[75] Inventors: Jeffrey K. Fergason, Menlo Park; Arthur L. Berman, San Jose; James L. Fergason, Atherton; John D. Fergason, Mountanview, all of Calif.

[73] Assignee: OSD Envizion Company, Menlo Park, Calif.

[21] Appl. No.: 89,265

[22] Filed: Jul. 9, 1993

Related U.S. Application Data

[63] Continuation-in-part of Ser. No. 814,380, Dec. 26, 1991, abandoned.

[51] Int. Cl.[6] .................................................. G02F 1/1335
[52] U.S. Cl. .............................. 359/53; 359/63; 359/73
[58] Field of Search .......................... 359/53, 63, 73

[56] References Cited

U.S. PATENT DOCUMENTS

| | | | |
|---|---|---|---|
| H686 | 10/1989 | Mullins | 359/37 |
| Re. 29,684 | 6/1978 | Gordin | 359/84 |
| Re. 32,521 | 10/1987 | Fergason | 359/36 |
| 2,423,320 | 7/1947 | Hurley | 2/8 |
| 2,548,230 | 4/1951 | Molyneux | 219/147 |
| 2,761,046 | 8/1956 | Herrick et al. | 2/8 |
| 3,137,784 | 6/1964 | Kasemann | 219/147 |
| 3,159,844 | 12/1964 | Haboush | 2/8 |
| 3,254,315 | 4/1966 | Marks et al. | 359/254 |
| 3,597,043 | 8/1971 | Dreyer | 359/74 |
| 3,731,986 | 5/1973 | Fergason | 359/85 |
| 3,873,804 | 3/1975 | Gordon | 219/147 |
| 3,881,808 | 5/1975 | Gurtler et al. | 359/40 |
| 3,890,628 | 6/1975 | Gurtler | 359/40 |
| 3,918,796 | 11/1975 | Fergason | 359/63 |
| 3,967,881 | 6/1976 | Katano et al. | 359/53 |

(List continued on next page.)

FOREIGN PATENT DOCUMENTS

| | | |
|---|---|---|
| 0157744 | 9/1985 | European Pat. Off. . |
| 55-92276 | 7/1980 | Japan . |
| 60-53934 | 3/1985 | Japan . |
| 60-63934 | 3/1985 | Japan . |
| 62-9319 | 1/1987 | Japan . |
| 1102523 | 4/1989 | Japan . |
| 76086909 | 2/1979 | Sweden . |
| 9214183 | 8/1992 | WIPO . |
| 9216820 | 10/1992 | WIPO . |
| 9313449 | 7/1993 | WIPO . |
| 9313397 | 7/1993 | WIPO . |

OTHER PUBLICATIONS

Sharp, et al, "Continuously Tunable Smectic A Liquid–Crystal Color Filter, May 1990", Optics Letters, v. 15, No. 10, pp. 523–525.

*Primary Examiner*—William L. Sikes
*Assistant Examiner*—Ron Trice
*Attorney, Agent, or Firm*—Renner, Otto, Boisselle & Sklar

[57] ABSTRACT

A welding helmet and lens therefor includes a shield and a lens including a two identical optical components, each including a polarizer, a further polarizer (analyzer) optically between said optical components and effectively shared as an output device from one optical component and an input device for the other optical component, the transmissive axes of respective polarizers of said optical components being operatively oriented relative to one another to improve extinction of light incident on said lens at prescribed angles. The lens may be used in other optical systems. A method of making a light transmission controlling optical system employing two optical components control device, includes assembling a plurality of identical optical components, each having substantially identical alignment characteristics, positioning at least two of the optical components in optical series such that at least one optical component is facing in a direction opposite the facing direction of the other optical component, whereby the polar alignment of at least one part of both of said optical components is equi-angular and opposite sense relative to a reference direction.

48 Claims, 6 Drawing Sheets

U.S. PATENT DOCUMENTS

| | | | |
|---|---|---|---|
| 4,019,808 | 4/1977 | Scheffer | 359/53 |
| 4,039,254 | 8/1977 | Harsch | 359/53 |
| 4,071,912 | 2/1978 | Budmiger | 359/66 |
| 4,155,122 | 5/1979 | Budmiger | 2/8 |
| 4,240,709 | 12/1980 | Hornell | 359/53 |
| 4,385,806 | 5/1983 | Fergason | 359/39 |
| 4,436,376 | 3/1984 | Fergason | 359/40 |
| 4,540,243 | 9/1985 | Fergason | 359/53 |
| 4,560,239 | 12/1985 | Katz | 359/52 |
| 4,728,173 | 5/1988 | Toth | 359/63 |
| 4,838,663 | 6/1989 | Lagerwall et al. | 359/64 |
| 4,844,569 | 7/1989 | Wada et al. | 359/73 |
| 5,187,603 | 2/1993 | Bos | 359/73 |
| 5,208,688 | 5/1993 | Fergason | 359/53 |

EYE PROTECTION DEVICE FOR WELDING HELMETS WHICH REDUCES OBLIQUELY INCIDENT LIGHT

This is a continuation-in-part of U.S. patent application Ser. No. 07/814,380, filed Dec. 26, 1991, now abandoned the entire disclosure of which hereby is incorporated by reference.

TECHNICAL FIELD OF THE INVENTION

The present invention relates generally, as is indicated, to the control of transmission of electromagnetic energy, especially for controlling transmission of light, and, more particularly, the present invention relates to improvements in controlling light transmitted through a lens in an eye protection device, such as a welding helmet or the like, whether the source of the light is located directly in front of the device or located oblique to the device.

BACKGROUND OF THE INVENTION

Welding helmets have been used in the past to protect the eyes and face of a person doing welding (hereinafter referred to as a welder) from the very bright light occurring during welding, e.g., emanating from the welding are, and from possible particles that may be flung toward the welder during welding. Early welding helmets had a lens through which a welder would view the work being welded and a protective shield material, such as metal, plastic or other solid material, that contained the lens and protected the welder's face from the light emitted by the welding operation and from particles. Typically the lens was a material that would transmit a relatively small amount of the incident light and, thus, when the welding was occurring would permit enough light to pass to the welder's eyes to observe the welding operation while blocking a substantial amount of the light occurring during welding so that the eyes would not be injured. Sometimes the lens was used in spectacle frames for eye protection without the face protecting shield.

Early welding helmets suffered from the disadvantage that the lenses were of fixed light transmission characteristic, i.e., darkness. Since the lenses were adequately dark (non-transmissive of or able to block transmission of some light) to perform eye protection function, it was difficult or even impossible in the absence of the welding arc to see through the lens such as to start a welding torch, arc, etc.

Efforts were made to provide variable light transmission characteristics in welding lenses and/or in welding helmets using such lenses. Several examples included variable mechanical devices, such as mechanical shutters located over the viewing area of the welding helmet to control the aperture through which light may be transmitted to the eyes of the welder. Sensors detected the occurrence of the welding light and caused a circuit automatically to close the shutter aperture.

Another early mechanical shutter used relatively rotatable polarizers in optical series. Depending on the brightness or "clearness" desired (or darkness or light attenuation desired) one polarizer was rotated relative to the other. A sensor for detecting incident light and a circuit responsive to the sensor controlled the relative rotation of the polarizers.

An example of a variable solid crystal welding lens with polarizers in protective eye glasses (spectacles) or goggles is disclosed in Marks et at. U.S. Pat. No. 3,245,315.

Other efforts made to provide variable light transmission characteristics for a welding lens have used variable liquid crystal light shutter devices. Two examples of twisted nematic liquid crystal cells used in welding lens assemblies in welding helmets are disclosed in U.S. Pat. Nos. Re. 29,684 (Gordon) and 4,039,254 (Harsch). In the Gordon light shutter a twisted nematic liquid crystal cell, sandwiched between crossed polarizers, rotates the plane of polarized light received from one polarizer to pass it through the second polarizer, thus allowing a welder to see in the absence of a welding arc. In response to welding light being detected by a sensor, a circuit energizes the twisted nematic liquid crystal cell so that polarized light remains unrotated and crossed polarizers block light transmission. In Harsch minimum light transmission occurs in the deengergized (dark) state and maximum transmission occurs when the liquid crystal cells are energized (clear state). In Harsch three polarizers and two twisted nematic liquid crystal cells are arranged such that residual leakage of light through the upstream pair of polarizers and liquid crystal cell when minimum transmission is intended will be reduced by cooperation with the downstream liquid crystal cell and the further polarizer without substantially reducing transmission when in the clear (energized) state.

Alignment of three parallel directionally aligned polarizers and two twisted nematic liquid crystal cells (the five being arranged alternately in tandem to provide selective control of light transmission) also is disclosed in Fergason U.S. Pat. No. 3,918,796.

In such a twisted nematic liquid crystal cell, e.g., as is disclosed in U.S. Pat. Nos. Re. 29,684 and 4,039,254, nematic liquid crystal is located between a pair of generally fiat plates which are pretreated at a respective surface of each by parallel rubbing or by some other process to obtain generally parallel structural alignment (alignment of the directors) of the liquid crystal material relative to the rub direction. The plates are placed in parallel to each other such that the rub direction of one surface is perpendicular to the rub direction of the other, and the liquid crystal material between the plates tends to assume a helical twist. During use, the twisted nematic liquid crystal cell is placed between a pair of plane polarizers (also referred to as linear polarizers). Light incident on the first polarizer is linearly polarized thereby and directed through the twisted nematic liquid crystal cell to the second polarizer. In the absence of an electric field input to the twisted nematic liquid crystal cell, the plane of polarization is rotated, for example, ninety degrees as the light is transmitted through the cell. Such light transmission through a twisted nematic liquid crystal cell sometimes is referred to as wave guiding of the light. In the presence of an electric field sufficient to cause alignment of substantially all of the liquid crystal material in the cell with respect to such field, the plane polarized light incident on the cell is transmitted therethrough without such rotation. Depending on the orientation of the second polarizer (also sometimes referred to as the analyzer or analyzer polarizer) relative to the first polarizer, polarized light will be transmitted or blocked, as a function of alignment of the liquid crystal material in the cell and, thus, of whether or not electric field is applied. The light transmission and the control of light transmission usually is substantially the same for any wavelength of the light.

A surface mode liquid crystal cell, which is still another type of liquid crystal cell, and devices using such a cell are disclosed in U.S. Pat. Nos. 4,385,806, 4,436,376, Re. 32,521, and 4,540,243. In contrast to the wave guiding type operation of a twisted nematic liquid crystal cell, the surface mode liquid crystal cell operates on the principle of optical retardation, and, in particular, it operates to retard one of the two quadrature components (sometimes referred to as ordinary ray and extraordinary ray, respectively) of plane polarized light relative to the other. Thus, a surface mode liquid crystal cell effectively can rotate the plane of polarization of plane polarized light by an amount that is a function of a prescribed input, usually an electric field. A surface mode liquid crystal cell in effect is a variable optical retarder or variable wave plate that provides retardation as a function of the prescribed input. By locating the surface mode cell between plane polarizers, the transmission of light through a device including the surface mode cell can be controlled. An example of a surface mode cell used in an eye protection device is found in U.S. patent application Ser. No. 07/653,661. Another surface mode type liquid crystal cell is described in U.S. Pat. No. 4,582,396.

While these devices which employ polarizers to provide variable light transmission characteristics are improvements over devices offering fixed light transmission characteristics or mechanical shutter controlled variable light transmission, they suffer from an inability to control adequately the transmission of light obliquely incident on the welding lens, such as that emanating from a welding are adjacent the welder. Such adjacent welding are may be from welding equipment operated by another individual who is carrying out welding adjacent the location at which the first-mentioned welder is carrying out welding. While crossed or operatively crossed polarizers provide a high rate of extinction for light which is incident on the lens normal to the lens or at oblique angles lying substantially along the planes of polarization of the crossed polarizers, extinction at others regions may be substantially less, thus potentially causing annoyance or discomfort to the eyes of the welder from light sources falling in these regions.

As will be described further below, the present invention is directed to a variable optical transmission controlling device which offers optical extinction over a wide range of incident angles. The device is described in detail with respect to use in a welding helmet. However, it will be appreciated that the device may be employed in other environments and in other devices and systems for controlling transmission of electromagnetic energy broadly, and, in particular, optical transmission. As used herein with respect to the preferred embodiment, optical transmission means transmission of light, i.e., electromagnetic energy that is in the visible spectrum and which also may include ultraviolet and infrared ranges. The features, concepts, and principles of the invention also may be used in connection with electromagnetic energy in other spectral ranges.

The invention is especially useful for eye protection wherein protection is desired for light incident on the eye from any angle. Exemplary uses are in welding helmets, spectacles, goggles, and the like, as well as safety goggles for nuclear flash protection, for protection from hazards experienced by electric utility workers and for workers at furnace and electrical plant areas and at other places where bright light that could present a risk of injury may occur. The invention may be used in other devices and applications in which light attenuation is desired.

Shade number or shade is the characterization of darkness of a welding lens (sometimes referred to as a welding filter or simply a lens), for example, a larger shade number represents a darker, more light blocking (or absorbing) or less optically transmissive lens and a smaller shade number represents a less dark, less light blocking (or absorbing) or more optically transmissive lens. Generally optical transmission means transmission of light and the image or view carried by the light without substantial distortion of those images, e.g., due to scattering. Shade number is a term of art often used in the field of welding and especially welding lenses for eye protection.

Clear state or clear shade means the state of highest operating luminous transmittance (or light transmission) of the lens. This state corresponds to the state having the lowest shade number for the lens.

Dark state or dark shade is the lowest operating luminous transmittance (or light transmission) of the lens. This state corresponds to the state having the highest specified shade number for the lens. The invention is described below in some instances indicating that in the dark state no light is transmitted. While this may be desirable for some applications of the principles of the invention, it will be appreciated that for a welding lens in the dark state there will be some transmission so that the welder can see to do the welding while some light is blocked to provide the desired eye protection from damage, injury or the like by the light emitted during welding.

Intermediate state or intermediate shade is one that is not the clear state and the dark state. It may be between the clear state and the dark state, but this is not always necessary, for it may even be darker than the dark state if such operation could be achieved. According to the described embodiment of the invention, the intermediate state provides an intermediate level of light transmission/absorption, i.e., between the clear state and the dark state, and occurs during power failure, inadequate power, or power off status of the lens.

Power failure, failure, or fail state means absence of power being delivered to the lens. Power failure also may mean that inadequate power is being delivered to the lens to cause it to assume the desired state.

Off state is the condition of the lens when no electrical power is being supplied to the lens; the off state also is referred to as the power-off state. As is described below, the intermediate shade preferably occurs in the welding lens during the off state. The fail state of the lens also is the off state, i.e., no power is provided due to failure of the power supply; and the fail state also may occur when there simply is inadequate power available to drive or to energize the lens to the clear state and dark state.

Shutter response time is the time required for the circuitry associated with the lens to detect a sharp increase in incident light (e.g., due to striking of the welding arc, etc.) and to switch the lens from the clear state to the dark state.

Shutter recovery time is the time required for the circuitry associated with the lens to detect a sharp decrease in light (e.g., due to extinguishing of the welding arc, etc.) and to switch the lens from the dark state to the clear state.

Variable transmittance is the ability of the lens to be switched from one level of luminous transmittance (also referred to as transmission of light) to another level of luminous transmittance in response to a change in incident illumination.

Dynamic operational range or dynamic optical range is the operational range of the lens between the dark state and the clear state, e.g., the difference between the shade numbers of the dark state and the clear state.

The entire disclosures of all of the above-mentioned patents and patent applications are hereby incorporated by reference.

BRIEF SUMMARY OF THE INVENTION

The present invention provides a light transmission controlling device suitable for use as eye protection, such as in a welding lens, which improves the contrast ratio between dark and clear states for light incident on the device from many angles.

In accordance with one embodiment of the invention a light transmission controlling device includes a first polarizer and a first analyzer in optical series having transmissive axes oriented substantially operationally orthogonal to one another, and a second polarizer and a second analyzer in optical series having transmissive axes oriented substantially operationally orthogonal to one another, the second polarizer and the first analyzer being in optical series and having their transmissive axes oriented substantially at 45 degrees to one another.

In accordance with another aspect of the invention, a light transmission controlling device includes a first optical component including in optical series a first polarizer, first means for rotating the plane of polarization of incident light as a function of a prescribed input, and a first analyzer, the transmissive axes of the first polarizer and the first analyzer being oriented to substantially block the transmission of light through the first optical component when the means for rotating is in a minimally rotating state, and a second optical component including in optical series a second polarizer, second means for rotating the plane of polarization of incident light as a function of a prescribed input, and a second analyzer, the transmissive axes of the second polarizer and the second analyzer being oriented to substantially block the transmission of light through the second optical component when the second means for rotating is in a minimally rotating state, the transmissive axis of the second polarizer being oriented at 45 degrees with respect to the transmissive axis of the first analyzer.

In accordance with a further aspect of the invention, a light transmission controlling device includes a first optical component including in optical series a first polarizer, first means for rotating the plane of polarization of incident electromagnetic energy as a function of a prescribed input, and a first analyzer, the transmissive axes of the first polarizer and the first analyzer being oriented to substantially block the transmission of light through the first optical component when the means for rotating is in a minimally rotating state; and, a second optical component including in optical series a second polarizer, second means for rotating the plane of polarization of incident electromagnetic energy as a function of a prescribed input, and a second analyzer, the transmissive axes of the second polarizer and the second analyzer being oriented to substantially block the transmission of light through the second optical component when the second means for rotating is in a minimally rotating state, the transmissive axis of the second polarizer being oriented at an angle with respect to the transmissive axis of the first analyzer to provide high contrast at predetermined incident angles.

According to an aspect of the invention, a light transmission control includes polarizer means for controlling light transmission to provide in at least one field of view a relatively dark area and a relatively less dark area, and further polarizer means for cooperating with the polarizer means to darken at least part of the relatively less dark area within the field of view.

According to another aspect, eye gear for protecting the eye of an individual, for example, includes a light transmission control having polarizer means for controlling light transmission to provide in at least one field of view a relatively dark area and a relatively less dark area, and further polarizer means for cooperating with the polarizer means to darken at least part of the relatively less dark area within the field of view; and mounting means for mounting the light transmission control for eye protection.

According to another aspect, a light transmission control includes polarizer means for controlling light transmission, including a polarizer and an analyzer operatively related and positioned relative to each other to control transmission of light therethrough, the light transmission appearing in a field of view relative to the polarizer means as having relatively more transmissive and less transmissive areas; and further polarizer means cooperative with the first polarizer means for increasing the uniformity of the darkness in relevant areas of the field of view, the further polarizer means comprising a further polarizer operatively related and positioned relative to the polarizer such that the respective transmissive axes of the polarizer and further polarizer are at other than parallel relation.

According to still another aspect a light transmission control includes polarizer means for controlling light transmission, including a polarizer and an analyzer operatively related and positioned relative to each other to control transmission of light therethrough, the light transmission appearing in a field of view relative to the polarizer means as having relatively more transmissive and less transmissive areas; and further polarizer means cooperative with the first polarizer means for increasing the total amount of area in the field of view having relatively dark light transmission characteristic.

According to yet another aspect, a light control device includes plural light polarizers, and switching means positioned relative to the light polarizers for switching the relative operational orientation of the respective transmissive axes of at least two of the polarizers, and the light polarizers consisting of only three plane polarizers.

Another aspect of the invention relates to a light transmission controlling device including three optical polarizers in optical series, each polarizer having a first side for receiving incident light and a second side, two of the polarizers being substantially identical having at least one similarly shaped physical wall (edge) and a transmissive axis oriented in the same direction relative to the physical wall, selectively operable switching means for changing the plane of polarization of light received from one of the polarizers and directing such light to another of the polarizers, and the two polarizers being relatively positioned with the physical walls thereof aligned in parallel overlying relation and the second surface of one polarizer facing the first surface of another polarizer whereby the direction of the transmissive axis of one polarizer is different from the direction of the transmissive axis of the other polarizer.

An aspect relates to a method of manufacturing a light transmission control device, including assembling a plurality of identical optical components, each having substantially identical alignment characteristics, positioning at least two of the optical components in optical series such that at least one optical component is facing in a direction opposite the facing direction of the other optical component, whereby the polar alignment of at least one part of both of the optical components is equi-angular and opposite sense relative to a reference direction.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed.

Although the invention is shown and described with respect to certain preferred embodiments, it is obvious that equivalents and modifications will occur to others skilled in the art upon the reading and understanding of the specification. The present invention includes all such equivalents and modifications, and is limited only by the scope of the claims.

DETAILED DESCRIPTION OF THE INVENTION

Figure 1:
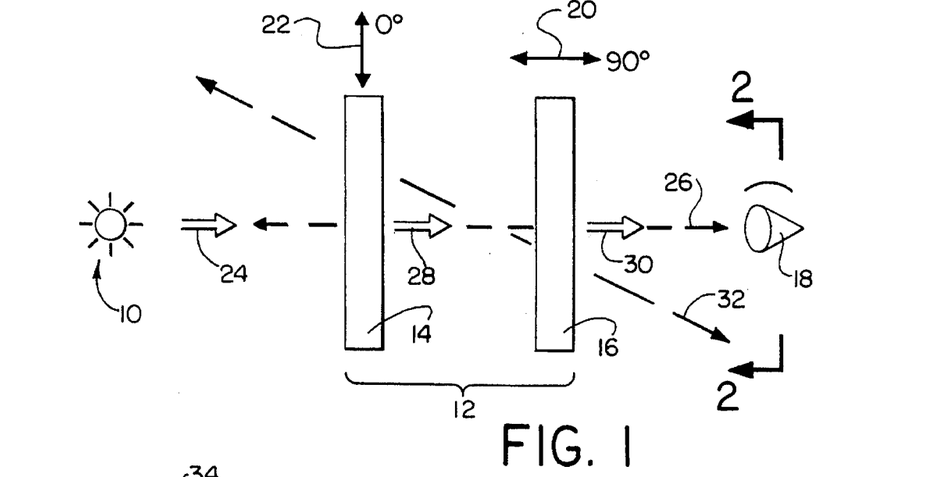
FIG. 1 is a schematic view of an optical system employing crossed polarizers, directions of polarization (axes of maximum light transmission) and/or of axes of various optical elements are indicated by arrows pointing up indicating relatively vertical or angularly indicating at an angle relative to vertical and/or to horizontal, and/or by "X" indications representing direction into the plane of the paper, the same convention being employed in the other drawing figures.

Referring, now, in detail to the drawings, wherein like reference numerals designate like parts in the several figures, and initially to FIG. 1, there is shown an illustration of a light source 10, an optical system 12 including a pair of plane or linear polarizers 14, 16 in optical series and an eye 18 positioned to view the light transmitted by the optical system. The transmission axis of the polarizer 16 (sometimes referred to as the transmissive axis), indicated by the arrow 20, operatively is oriented relative to the transmissive axis of the first polarizer 14, indicated by the arrow 22, at angle of 90 degrees. Such an operative 90 degree orientation can be effected by actually orienting the respective transmissive axes of the polarizers at a 90 degree angle or by orienting the polarizers by some angle such that a material located between the polarizers effectively rotates the plane of polarization of light leaving the first polarizer to impinge upon the downstream polarizer at a 90 degree angle to its transmissive axis when the system is operating in its optically off state. A second polarizer following a first polarizer in optical series is referred to as an analyzer, and thus the polarizer 16 will be referred to as an analyzer herein.

As an example of the functioning of the optical system 10, consider light rays 24 produced by the light source 10 which, if transmitted through the polarizer 14 and analyzer 16, would impinge upon an eye 18 located on an axis 26 projecting through the polarizer and analyzer substantially normal to the physical plane of the polarizer and analyzer and at a reasonable distance from the optical system. To impinge upon the eye 18 such light rays 24 would need to propagate substantially along the axis 26. A portion of the light rays 24 having a plane of polarization matching that of the transmissive axis of the first polarizer 14 will be transmitted through the first polarizer while the remaining portion of light rays having a resultant plane of polarization at a fight angle to the arrow 22 will be substantially blocked from transmission. The light rays 28 passing through the first polarizer will predominately have a plane of polarization in the direction of the arrow 22 corresponding to the transmissive axis of the first polarizer 14. The light rays 28 incident on the analyzer 16 will thus be substantially blocked from transmission by the analyzer since the plane of polarization of the light rays 28 are normal to the transmissive axis (indicated by arrow 20) of the analyzer. Consequently, the eye 18 viewing the optical system 12 will see a relatively uniformly dark analyzer 16 since, as a result of the distance from the optical system, the eye would detect only the light rays 24 from the light source 10 propagating substantially along the axis 26 and emerging from the optical system as rays 30 and these rays have been blocked by the crossed polarizer 14 and analyzer 16. Light rays propagating through the optical system 10 along a path at a substantial angle to the axis 26, for example along the axis 32, even if not blocked by the crossed polarizer 14 and analyzer 16, likely would not impinge upon the eye 18 and thus would not be seen by the eye 18.

Figure 2:
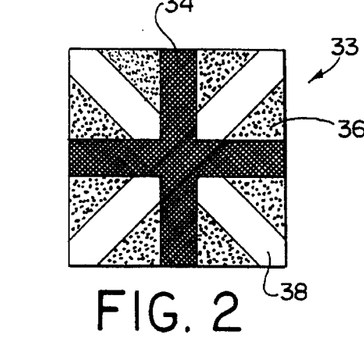
FIG. 2 is an illustration of the optical transmission pattern seen when viewing the optical system of FIG. 1 from a point near the optical system.

However, it has been found that if the eye 18 were positioned very near the optical system, say one or two inches behind the analyzer 16, the extinction of light by the optical system 12 will vary as a function of the incident rotational angle of the light around the axis 26, effectively forming a pattern 33 as shown in FIG. 2. In FIG. 2, the dark cross-hatched areas 34 of the pattern 33 represent regions of a high optical contrast ratio, i.e., regions of substantial attenuation in the dark state relative to the clear state; the stippled areas 36 represent regions of a medium optical contrast ratio; and the white areas 38 represent regions of a poor optical contrast ratio, i.e., regions of relatively high transmission intensity in both the dark and the clear states. The transmission pattern 33 results from the ability of the crossed polarizer and analyzer to attenuate effectively only light which is incident on the optical system along the axis 26 or at oblique angles to the axis 26 lying substantially along the transmissive axes of the crossed polarizer and analyzer. When the eye 18 is positioned near the optical system 12, incident light propagating through the system at angles other than along the axis 26, for example, along the axis 32, may impinge upon the eye and will thus be seen by the eye if not effectively attenuated by the crossed polarizer 14 and analyzer 16. As noted above when the eye is located at a reasonable distance, for example, at least several inches, from the optical system 12, light propagating through the device which would impinge upon the eye, if transmitted though the system, is that propagating substantially along the axis 26, and therefore at substantial viewing distances transmission intensity pattern of FIG. 2 does not occur.

Figure 3:
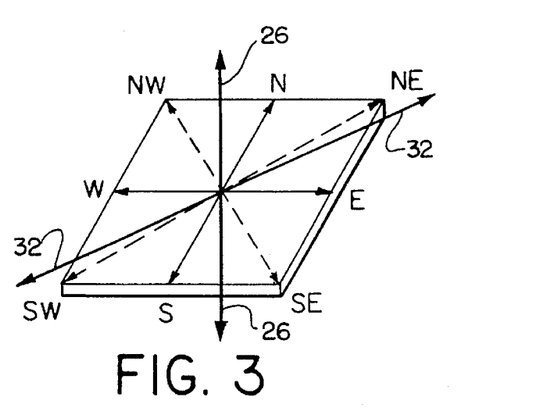
FIG. 3 is a map representation of incident angles projected on the surface of the optical system of FIG. 1.

Referring to FIG. 3 there are shown map coordinates imposed upon a surface of the optical system 12, such as the surface of the analyzer 16 facing the eye 18. The capital letters in the figure are attributed their well known designations, for example, N designates north, E designates east and NE designates northeast. The axis running between north and south corresponds to the transmissive axis 22 of the first polarizer 14 and the axis running east-west corresponds to the transmissive axis 20 of the analyzer 16. Referring to FIGS. 2 and 3 conjunctively, it is seen that the cross-hatched areas 34 of the highest contrast ratio lie substantially around the north-south and east-west axes corresponding to the transmissive axes of the polarizer 14 and analyzer 16, respectively. The white areas 38 of greatest transmission intensity lie substantially along axes running northeast-southwest and northwest-southeast, or at 45 degrees to the transmissive axes of the polarizers 14, 16. The stippled areas 36 of medium optical contrast ratio lie between the areas of greatest extinction 34 and the areas of very low contrast ratio 38.

Conventionally, in some instances two optical systems 12 have been combined in series, with the second optical system being rotated 90 degrees relative to the first so that only three polarizers need be employed. In these instances the light transmission through the systems is still substantially as illustrated by pattern 33, with light propagating through the areas 38 of least contrast ratio still not being adequately attenuated.

Consequently, for an optical protection device employing an optical system 12, light incident on the optical system 12 from a light source lying in the northeast-southwest or northwest-southeast regions 38 would propagate through the crossed polarizers of the optical system and impinge upon the eye 18 positioned within an inch or two of the optical system without the desired attenuation. In such an eye protection system, light incident on the protection lens from a source lying in the transmissive regions 38 may result in annoyance, discomfort or even injury to the eyes of the wearer. Further, in a welding lens application, the basic components of which will be described more fully below relative to the preferred embodiment, light impinging on the eyes of a welder from the arc of an adjacent welder located in a low contrast ratio region 38 of the device may be at a higher intensity than the light transmitted from the welder's own arc which latter light will propagate through the optical system substantially along the axis 26 and will be significantly attenuated. As a result of the relative brightness of the nearby arc in contrast to the welder's own arc, the ability of irises of the welder's eyes to adjust to the light from the welder's own arc will be greatly hampered thus impairing the view of the welding area.

Figure 4:
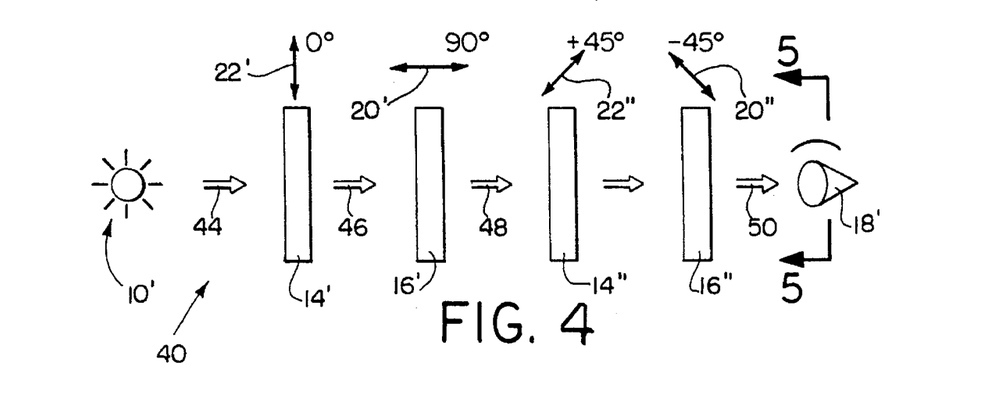
FIG. 4 is a schematic view of the polarizing components of an optical system oriented in accordance with the present invention.

Turning now to FIG. 4 there are shown the polarizing components for an optical system 40 in accordance with the present invention, a light source 10' providing incident light to the optical system and an eye 18' positioned near the optical system for viewing light transmitted through the system. Primed reference numerals designate parts of the drawings that are similar in function to parts designated by unprimed or multi-primed reference numerals. The transmissive axes 22', 20' of the first polarizer 14' and first analyzer 16', respectively, are oriented 90 degrees relative to one another as are the polarizers in the optical system 12 of FIG. 1. The transmissive axes 22", 20" of the second polarizer 14" and second analyzer 16", respectively, are also oriented 90 degrees relative to one another, but at 45 degree angles relative to the first polarizer 14' and first analyzer 16'. To explain in more detail, assume that the transmissive axis 22' of the first polarizer 14' is assigned an orientation angle of zero degrees. The transmissive axis 20' of the first analyzer 16' would thus be at 90 degrees relative to the transmissive axis of the first polarizer 14', and the transmissive axes 22", 20" of the second polarizer 14" and second analyzer 16" would be at orientations of 45 degrees and −45 degrees, respectively, to the transmissive axis of the first polarizer.

A light ray propagating from the light source 10' through the optical system 40 substantially along the axis 26' will be significantly attenuated by the pairs of crossed polarizers and analyzers 14', 16' and 14", 16" as was accomplished generally by the optical system 12. However, for light incident on the optical system 40 at oblique angles, the contrast ratio of the optical system 40 of the present invention is greatly improved. Consider a light ray 44 incident upon the optical system 40 from a light source 10' spaced from axis 26' and located approximately between the transmissive axes 22', 20' of the first polarizer 14' and first analyzer 16', respectively. The light ray 44 will propagate from the light source 10' toward the eye 18' and emerge from the first polarizer 14' as light ray 46 which will pass through the first analyzer 16' and emerge as light ray 48 substantially unattenuated since the angle of incidence of the light rays will lie in the region of least contrast ratio 45 degrees between the transmissive axes of the polarizer 14' and analyzer 16'. However, as the light ray 48 propagates through the second polarizer 14" and emerges to pass through the second analyzer 16", the angle of incidence will lie in either the transmissive axis of the second polarizer or the second analyzer. Consequently, it will be significantly attenuated by the second or righthand (relative to the drawing) set of the second polarizer and second analyzer before emerging from the optical system 40 as light ray 50 which impinges upon the eye 18'.

Figure 5:
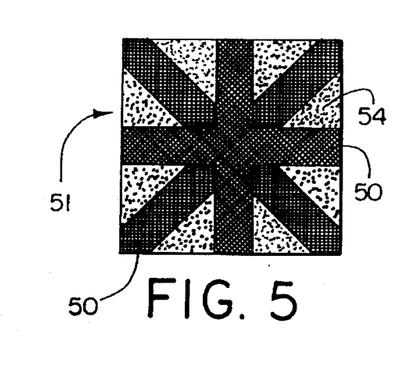
FIG. 5 is a illustration of the optical transmission pattern seen when viewing the optical system of FIG. 4 from a point near the optical system.

Referring to FIG. 5, there is shown a transmission intensity pattern 51 for the optical system 40 when viewed by an eye 18' located within one or two inches of the optical system. The dark cross-hatched areas 52 represent regions of a high optical contrast ratio, i.e., regions of substantial attenuation in the dark state relative to the clear state, and the stippled areas 54 represent regions of a medium optical contrast ratio. Adopting the map coordinates set forth in FIG. 3 to the transmission pattern 51 of FIG. 5, it is seen that a high contrast ratio is achieved along the northeast-southwest and northwest-southeast axes as well as along the north-south and east-west axes. The intermediate regions have a medium contrast ratio, and there are no areas that are substantially transmissive in comparison to the relatively large transmissive regions 38 for the conventional optical system 12.

Figure 6:
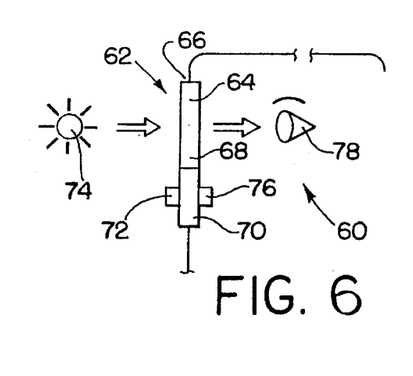
FIG. 6 is a schematic view of a welding helmet with a variable transmission liquid crystal lens in accordance with the present invention.

Turning now to FIG. 6, there is shown a welding helmet 60 according to the invention including a protective shield 62 and a filter assembly 64 mounted in the shield. The shield 62 may be of generally optically non-transmissive material, such as metal, plastic, or other material to protect a welder's face and/or head as is conventional. The filter assembly 64 may be permanently mounted in an opening 66 of the shield 62, or means (not shown) may be provided to hold the filter assembly 64 in the opening 66 and also to permit removal of the filter assembly from the shield, if desired.

The filter assembly 64 itself includes a welding lens 68 and a driving circuit 70 for supplying a prescribed input to the welding lens 68 to effect operation. Preferably that input is an electric field produced by a voltage from the driving circuit 70 suitable to operate a liquid crystal cell in the welding lens, as is described further below. However, it will be appreciated that the prescribed input may be other than an electric field, for example, a magnetic field, thermal energy, or some other prescribed input that will operate the welding lens 68.

The welding lens 68 is preferably of a type that can achieve three different optical states, namely a clear state, a dark state, and a third state (referred to below as an intermediate state) of optical transmission that is different from the clear state and the dark state. The intermediate state has a transmissive quality that is preferably darker than the clear state, and likely, but not necessarily, less dark than the dark states i.e., between the clear state and the dark state (as is described below in the illustrative examples of the invention). Moreover, the welding lens 68 preferably is of the type that assumes the intermediate state in the absence of power being supplied thereto by the driving circuit 70 or when the power level supplied is inadequate; assumes the clear state in the presence of a first electric field input, i.e., an electric field of a first magnitude; and assumes the dark state in the presence of a second electric field input, i.e., an electric field which is of greater magnitude than the first.

Although the preferred embodiment employs the lens 68 in a welding helmet 60, the lens may be used for other eye protection functions or other functions in accordance with the operative principles described herein. As will be appreciated, the lens provides control of the intensity of light transmitted therethrough, for example, to the eyes of a welder. Preferably such transmission is without degradation of the image characteristics of the transmitted light, thus, enabling an object, scene, etc. to be viewed without distortion. Moreover, it will be appreciated that although the lens of the invention preferably is used to protect the eyes of a person, it may be used to control transmission of electromagnetic energy for other purposes as well.

The driving circuit 70 includes a source of electric power, e.g., a storage battery, photovoltaic cell, transformer connection to some other power source (such as that available through an electrical receptacle), etc., and circuitry necessary to establish the requisite electrical field across the liquid crystal cell in the welding lens 68. A sensor or detector 72, which may be part of the driving circuit, is cooperative with the driving circuit to detect the intensity of incident light and to produce an electrical field having a voltage which is analog or step-wise proportional in amplitude to the intensity of such incident light. More particularly, when the intensity of light incident on the sensor 72 is less than that occurring during welding, the driving circuit 70 produces an electric field which energizes or drives the welding lens 68 to the clear state; and when light incident on the sensor 72 is representative of the occurrence of welding (e.g., commencing immediately upon striking of the welding arc represented at 74), the driving circuit 70 produces an electric field which energizes or drives the welding lens 68 to the dark state. An exemplary driving circuit is described in copending U.S. patent application Ser. No. 07/365,167, filed Jun. 12, 1989, the entire disclosure of which is incorporated by this reference. Other driving circuits also may be used and/or designed that perform the various functions energizing the liquid crystal lens in the described manner. Should the driving circuit fail such that power is not provided the welding lens in particular (or that provided is inadequate), the welding lens will assume the intermediate state or shade, as is described in further detail herein.

Using the welding helmet 60, a welder would press a power switch 76 to turn on the driving circuit 70 to energize the welding lens 68 to the clear state; and then the welder would place the helmet on his or her head generally aligning the welding lens 68 with the eyes 78. As a result of energizing the welding lens 68 to the clear state, the welder then can see through the welding lens to place the welding tools in proximity to a work piece intended to be welded. Upon the inception of welding, e.g, striking of the welding arc, the sensor 72 detects the same and causes the driving circuit 70 to energize the welding lens 68 to the dark state. The dark state is designed to protect the eyes of the welder from damage due to the electromagnetic emissions, in particular the intense light emitted during welding. In case the driving circuit 70 were to fail during use, the welding lens 68 would preferably promptly assume the intermediate state, which is sufficient to provide a measure of protection to the eyes of the welder until the welding action is terminated. The shield 62 and the filter assembly 64 preferably are adequately strong to protect the face of the welder from particulates possibly emitted during welding; and the shield itself also preferably is not optically transmissive so that it provides protection from electromagnetic energy for the face and eyes of the welder during welding.

Figure 7:
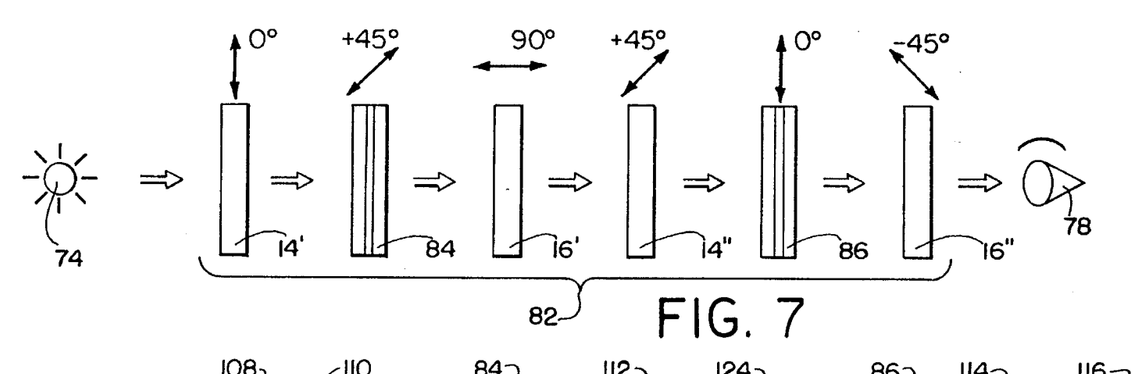
FIG. 7 is a schematic view of an embodiment of the light transmission control device of the welding lens of FIG. 6 using two surface mode liquid crystal devices having no residual retardation.

The welding lens 68 includes a controllable light transmission controlling device 82 as shown in FIG. 7 to protect the eyes 78 of a viewer from harm resulting from an unattenuated welding arc. The welding lens 68 may also include a bandpass filter (not shown) in optical series so that light from welding operation, e.g., emitted by a source 74, will have to pass through both the bandpass filter and the light transmission controlling device 82 before reaching the eyes 78 of the welder. Desirably the characteristics of the band pass filter and of the light transmission controlling device 82 are selected such that in the presence of a welding arc the amount of light transmitted to the eyes 78 of the welder in the power off or fail mode would not injure the eyes of the welder in case there is an accidental power off or power failure occurrence of the driving circuit 70, especially if upon realizing such power off or power failure occurrence the welder relatively promptly terminates the welding operation. Optically, it does not matter which of the filter or device 82 is closer to the welding arc source 74 and which is closer to the eyes 78. However, in the preferred embodiment the band pass filter is placed optically upstream (relative to the eyes 78) of the variable device 82. Since the filter preferably is not dynamic or actively changed, and, therefore, is less subject to damage than the device 82, since it preferably has a hard exterior surface, such as glass or quartz, etc., for strength and durability, and since it preferably blocks transmission of ultraviolet and infrared wavelengths of electromagnetic energy which are known to be damaging to at least some liquid crystal cells and/or materials thereof, this positioning will avoid subjecting the optically dynamic device 82 to unnecessary damage and may increase longevity. The cooperation of the bandpass filter and the light transmission controlling device 82 is described more fully in U.S. patent Ser. No. 07/653,661, the entire disclosure of which is incorporated by this reference.

The controllable light transmission controlling device 82 includes a first polarizer 14' and first analyzer 16' with their respective transmissive axes oriented orthogonally to one another and a second polarizer 14" and second analyzer 16" also with their respective transmissive axes oriented orthogonally to one another. The transmissive axes of the lefthand combination of the polarizer 14' and analyzer 16' are oriented at a 45 degree angle to the transmissive axes of the righthand combination of the polarizer 14" and analyzer 16" as discussed above relative to FIG. 4. In optical series between the first polarizer 14' and the first analyzer 16' is located a surface mode liquid crystal cell 84. A second surface mode liquid crystal cell 86 is also located in optical series between the second polarizer 14" and the second analyzer 16", respectively.

Figure 8A:
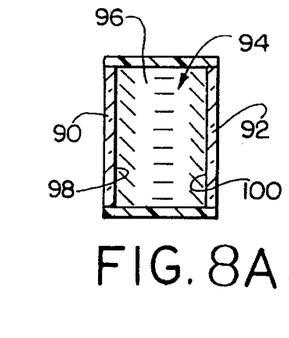
FIG. 8A is a sectional,schematic view of a 180 degree twist surface mode liquid crystal cell constructed with nematic liquid crystal material sandwiched between plates having rub (or alignment) directions which are parallel but which pretilt the average directors of the liquid crystal molecules located near the surfaces in an opposite rotational sense relative to the surfaces.
Figure 8B:
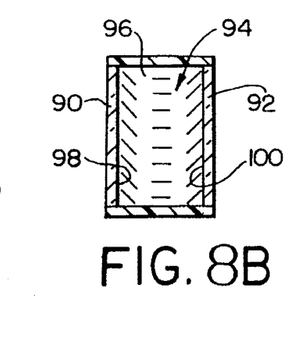
FIG. 8B is a sectional schematic view of a zero twist surface mode liquid crystal cell constructed with nematic liquid crystal material sandwiched between plates having rub (or alignment) directions which are parallel but which pretilt the average directors of the liquid crystal molecules located near the surfaces in a like rotational sense relative to the surfaces.

FIGS. 8A and 8B illustrate a sectional view of two types of surface mode liquid crystal cells which may be used in for the surface mode cells 84, 86. Each surface mode cell includes a pair of plates 90, 92, usually of glass, plastic or other polymer material, etc., preferably generally transparent to visible light, and positioned generally in parallel planar relationship. The plates 90, 92 define a volume 94 therebetween, which usually is sealed at the edges of the plates, containing liquid crystal material 96. The liquid crystal material 96 preferably is nematic liquid crystal material or operationally nematic liquid crystal material which has the desired optical, alignment, and operational characteristics of nematic liquid crystal. The nematic liquid crystal material has directors or structural alignment characteristics which are influenced by the interior surfaces 98, 100, of the plates confronting the liquid crystal material 96. Those surfaces 98, 100 preferably are pretreated, e.g., by rubbing in parallel direction or by some other means, or technique, one example being application of an evaporated or sputtered coating to cause alignment of the liquid crystal directors with such rub direction, as is known. Thus, rub direction or alignment direction sometimes are used interchangeably. Moreover, the plates 90, 92, are positioned so that the rub directions thereof are in the same direction (zero twist) as illustrated by FIG. 8B or in an opposite direction (180 degree twist) as illustrated in FIG. 8A (sometimes respectively referred to as parallel and anti-parallel surface mode cells). In the absence of a suitable electric field, the liquid crystal structure will tend to align generally in parallel with such rub directions. As is depicted schematically in FIGS. 8A and 8B, in the presence of a suitable electrical field or as a result of an electric field applied to the cell in a conventional manner, the average orientation directors of the liquid crystal molecules in the center portion of the cell, (i.e., center according to the thickness dimension of the volume between the plates) will align perpendicular to the plates 90, 92, and the directors near the surface will align generally in parallel to the surfaces providing birefringence, and, thus, retardation. In the presence of a larger (or otherwise suitable) electric field not only will the directors in the center of the cell be aligned generally perpendicular to the plates, but also directors of most of the liquid crystal nearer the surface also will align generally perpendicular to the plates except for in a relatively small region nearest the surfaces 98, 100 where the directors will remain somewhat parallel to the surfaces.

Returning to the discussion of the device 82 illustrated in FIG. 7, the surface mode cell 84 located between the first polarizer 14' and the first analyzer 16' is oriented with its rub direction at a 45 degree angle to the transmissive axes of the first polarizer and first analyzer. Such orientation, the birefringence characteristics of the liquid crystal material and the thickness of the surface mode liquid crystal cell, and, thus, the optical retardation provided thereby as it is electrically driven, preferably are selected generally to provide 90 degrees rotation of the plane of polarization or direction of polarization of incident plane polarized light in one operative mode. In the other operative mode such surface mode liquid crystal cell provides in the optimized case substantially no retardation (other than a small residual amount) and, thus, no rotation of plane of polarization if incident plane polarized light. Likewise, the surface mode cell 86 located between the second polarizer 14" and the second analyzer 16" is oriented with its rub direction at a 45 degree angle to the transmissive axes of the second polarizer and second analyzer. Consequently, the lefthand set of the second polarizer 14", the surface mode cell 86 and the second analyzer 16" is essentially a copy of the righthand set of the first polarizer 14', the surface mode cell 84 and the first analyzer 16' but rotated by 45 degrees around an axis projecting through the optical system 40.

When an ideal surface mode cell 84 is fully energized it will impart no retardation on the light passing therethrough. Therefore plane polarized light emerging from the first polarizer 14' will have a polarization direction orthogonal to the transmissive axis of the first analyzer 16' and will be substantially blocked from transmission. The optically identical right hand components of the optical system will further attenuate the light leaking through the lefthand optical components. Further, since the righthand optical components are oriented at a 45 degree angle to the lefthand optical components the optical system will achieve the improved attenuation characteristics for obliquely incident light described above relative to FIG. 4.

Figure 8C:
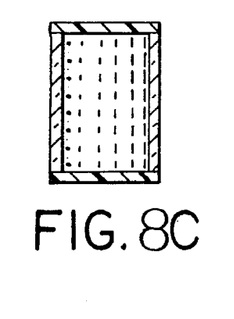
FIG. 8C is a sectional schematic view of a twisted nematic liquid crystal cell constructed with nematic liquid crystal material sandwiched between plates having rub (or alignment) directions which are oriented at 90 degrees relative to one another.

The sectional view of the liquid crystal cell shown in FIG. 8C is that of a conventional twisted nematic liquid crystal cell which can be substituted for the surface mode cells 84, 86 employed in FIG. 7 and discussed above. In its nonenergized state the liquid crystal within a twisted nematic liquid crystal cell assumes a helical twist alignment which guides light incident on the cell through a 90 degree rotation. In the presence of an electric field the liquid crystal aligns with the electric field and no rotation of the incident light occurs. In most cases a twisted nematic liquid crystal cell is slower to operate in response to an electric field intended to drive it to the state that it does not rotate polarization than a surface mode type liquid crystal cell, although such slower operation may be acceptable for some applications of the invention.

The liquid crystal devices shown in FIGS. 8A, 8B and 8C are exemplary devices that may be used selectively or controllably to rotate the plane of polarization of incident plane polarized light. Other devices also may be used, depending on the speed of response, other optical characteristics, etc desired.

Figure 9:
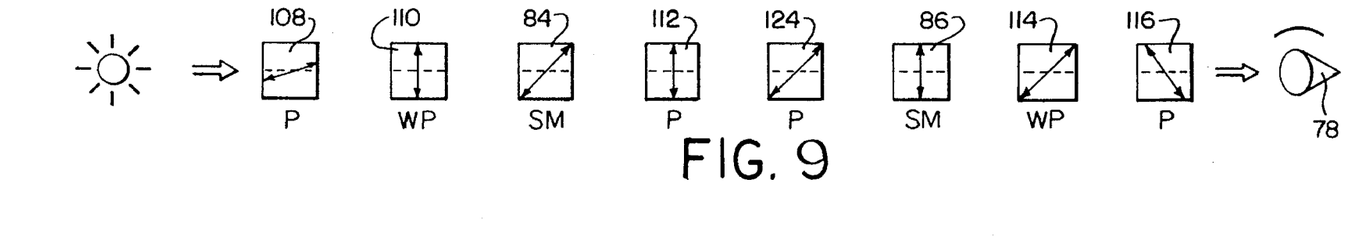
FIG. 9 is a schematic view of a transmission control device similar to that of FIG. 7 but additionally including compensation for the residual birefringence of the surface mode cells.

FIG. 9 is a schematic view of a transmission controlling device similar to that of FIG. 7 but additionally including wave plates which compensate for the residual birefringence of the surface mode cells 84, 86. The surface mode cell 84 when in its fully energized state, or when effectively not retarding, has a small residual birefringence as a result of the liquid crystal molecules near the plates not fully reorienting generally normal (perpendicular) to the plates in the cell energized state. Due to that residual birefringence there will be a small amount of optical retardation in the fully energized condition. To compensate for this residual birefringence, and, thus, to maximize the dark shade of he device when so driven, the first polarizer 108 is offset from being truly orthogonal to the transmissive axes of first analyzer 112 and wave plate 110 is inserted in optical series between the polarizer 108 and surface mode cell 84. The amount of offset depends on the amount of residual birefringence of the surface mode cell (which usually is a function of the voltage at which the surface mode cell is intended to be driven in the high voltage nonretarding state). In the lefthand four optical components the polarizer 108 and the waveplate 110 provide the surface mode cell 84 with elliptically polarized light and the surface mode cell 84 when fully energized provides the analyzer 112 plane polarized light that is substantially, preferably fully, orthogonal to the transmissive axis of the analyzer 112. In the righthand segment of the optical system the wave plate 114 and analyzer 116 are optically downstream of surface mode cell 86 and provide compensation for residual birefringence thereof in essentially the same manner as is performed in the lefthand segment.

Figure 10:
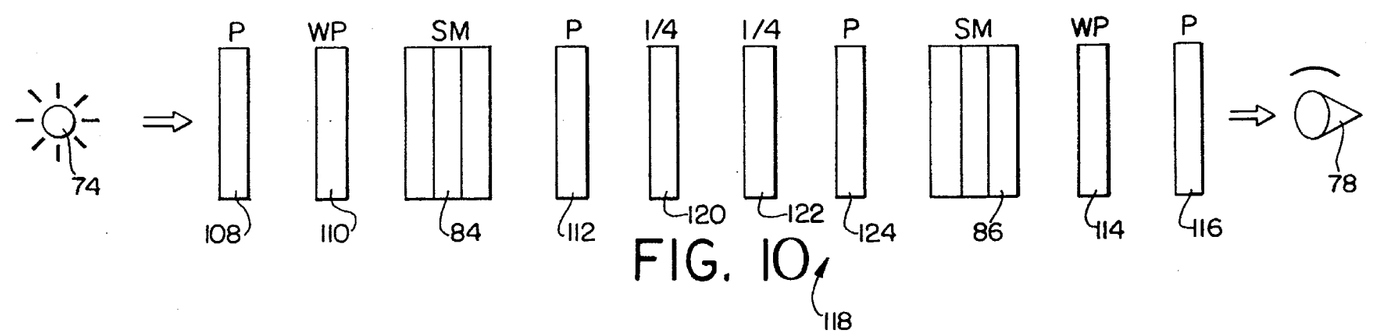
FIG. 10 is a schematic view of a transmission control device similar to that of FIG. 9 but including two wave plates (preferably quarter wave plates) to improve optical transmission in the optically on clear state.

The optical system 118 of FIG. 10 is virtually identical to the optical system of claim 9 with the addition of two wave plates 120, 122 (which preferably are quarter wave plates). In the embodiment of figure 9 the transmissive axes of the first analyzer 112 and the second polarizer 124 are by necessity, to accomplish the goals of the present invention, oriented 45 degrees relative to each other. This 45 degree crossed relation results in further attenuation of light transmitted through the optical system of FIG. 9 which may be acceptable for welding and similar applications. In other applications where light transmission in the optically on or clear state is to be maximized the quarter wave plates 120, 122 inserted between the left and righthand optical components shown in FIG. 9 eliminates the loss due to the 45 degree rotation of the righthand optical components relative to the lefthand optical components. In this regard the quarter wave plates may be considered an optical coupler. The first quarter wave plate 120 is oriented at 45 degrees relative to the transmissive axis of first analyzer 112, and the second quarter wave plate is oriented with its axis being 45 degrees relative to the transmission axis of second polarizer 116. The first quarter wave plate 120 converts incident plane polarized light from analyzer 112 to circularly polarized light and the second quarter wave plate 122 converts incident circular polarized light to plane polarized light having a polarization axis parallel to the transmissive axis of the second polarizer 124.

Figure 11:
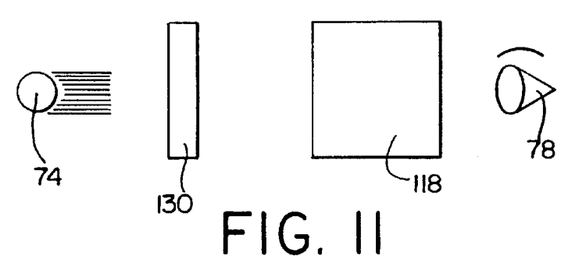
FIG. 11 is the optical system of FIGS. 7, 9 or 10 with the addition of a wave plate (preferably a quarter wave plate) placed optically before the remainder of the system to ensure that the first polarizer in the optical system attenuates at least a portion of the incident light.

The optical system of FIG. 11 includes the optical components of either FIG. 7, 9 or 10 with the addition of a wave plate 130 before the remainder of the components. The waveplate 130, which is preferably a quarter wave plate, ensures that light incident on the optical system of FIG. 7, 9 or 10 will have a component that is oriented orthogonal to the first polarizer. In the event that plane polarized light was directed upon the optical system having a plane of polarization matching the transmissive axis of the first polarizer, the wave plate 130 would elliptically polarize the light or subdivide the light into its quadrature components (e.g., ordinary and extraordinary ray components) so that at least a portion of the light is blocked from transmission by the first polarizer.

The invention is described herein as undergoing certain operation in response to a prescribed input. The preferred prescribed input is an electric field. However, it will be appreciated that other prescribed inputs may be used, and reference to electric field may include equivalently such other prescribed inputs. For example, as is known, liquid crystal cells are responsive to magnetic field inputs and to thermal inputs. Other inputs also may be possible to obtain generally equivalent operation. Also, although specific alignments of components are identified, such as a 45 degree or 90 degree relationship, these are optimized relationships. The alignments of the lefthand polarizer-analyzer combination relative to the righthand combination may be offset, however, by other than 45 degrees. In circumstances where the source of incident light is predictable, the righthand polarizer-analyzer combination may be offset from the lefthand combination to provide high contrast in that region. For instance, the righthand polarizer-analyzer combination may be offset by, say, 20 degrees from the lefthand combination to broaden the north-south and east-west high contrast portions of the light transmission pattern to provide protection in those regions.

It will also be appreciated that although several embodiments have been described herein, the various features disclosed in one embodiment and/or drawing figure, may be employed in the other embodiments and/or drawing figures.

Additionally, it will be appreciated that the crossed relationship of two sets of crossed polarizer and analyzer are described, more than two sets, such as three sets, also may be used in which case each set may be aligned at other than 45 degrees to each other, say with the first set at 0 degrees, the second set at 30 degrees rotation relative to the first set, and the third set at 60 degrees rotation relative to the first set, etc.

Although the invention is described with respect to a physically crossed polarizer and analyzer relation (90 degrees to each other) in each of the two sets thereof, the features of the invention may be employed when the polarizer and analyzer of one or both sets are operationally crossed but not physically crossed. Operationally crossed may mean that the polarizer and analyzer are physically not crossed, e.g., they are oriented with the transmissive axes thereof at other than a 90 degree relation, such as in parallel (0 degree relation) or some other relation; and some means, such as a surface mode liquid crystal cell and/or other means may be used to effect optical rotation of the plane of polarization of light received from the polarizer to have its plane of polarization or direction of polarization oriented at 90 degrees to the transmissive axis of the analyzer.

Figure 12A:
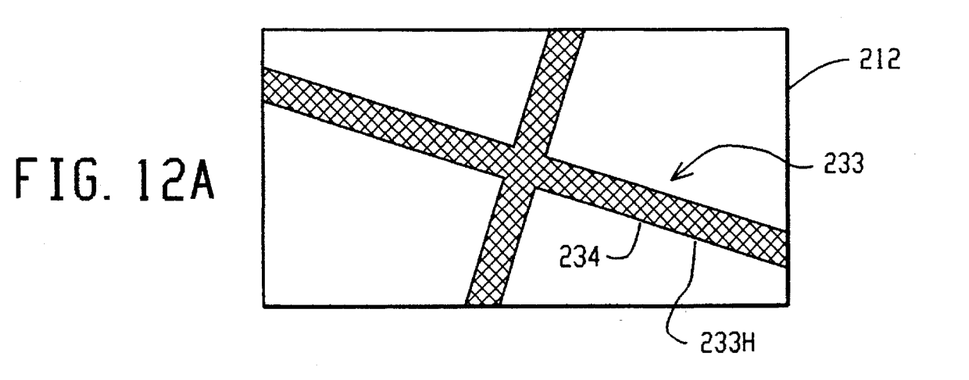
FIG. 12A is a schematic illustration of a field of view with areas of relatively minimum light transmission obtained by two cooperative polarizers.
Figure 12B:
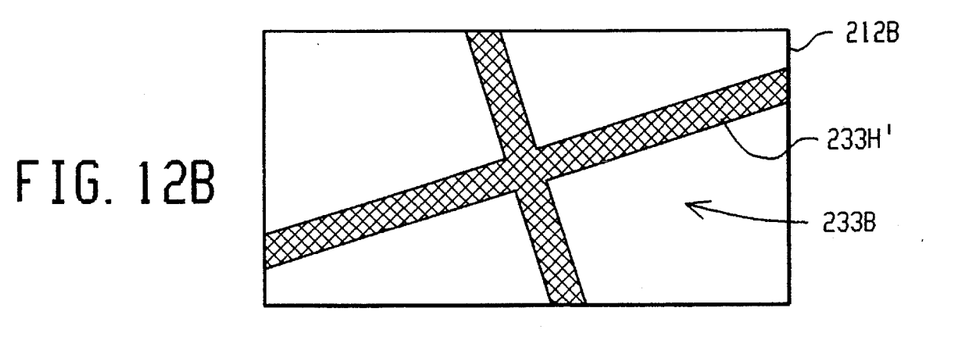
FIG. 12B is a schematic illustration of a field of view with areas of relatively minimum light transmission obtained by two cooperative polarizers.

FIG. 12A is an example of the field of view 212 of an optical system (also referred to herein as a shutter), similar to the optical system 12 of FIG. 1, including a pair of plane or linear operationally crossed polarizers. The optical system 212 has a pattern 233 representing the relatively more substantial extinction of light or minimal light transmission, e.g., as the pattern 33 of FIG. 2. The dark cross-hatched areas 234 of the pattern 33 represent regions of relatively high contrast ratio, e.g., regions of substantial attenuation in the dark state relative to the clear state when the optical system 212 is used, for example, as a substitute for the optical system 12 of FIG. 1. The pattern 233 has a relatively horizontal, i.e., relative to horizontal of the drawing of FIG. 12A, portion 233H that is at an angle nearly horizontal, but is not horizontal. An example is an angle of about 20° (twenty degrees) from horizontal. Such angle is not intended to be limiting. FIG. 12B is an example of the field of view 212B of an optical system similar to the optical system providing the field of view 212; but the nearly horizontal portion 233H' of relatively dark pattern 233B is tilted relative to horizontal about the same amount but in the opposite direction as the horizontal portion 233H of the pattern 233B.

The patterns 233, 233B of FIGS. 12A and 12B respectively are formed by cooperative pairs of linear polarizers as was the case in the optical system 12. The cooperative pairs of linear polarizers may include, for example, two polarizers forming the first pair to create the pattern 233 and two additional polarizers forming the second pair to create the pattern 233B, e.g., as was described above with respect to the embodiment of FIG. 4. Alternatively, the cooperative pairs of linear polarizers may share one of the polarizers so that only three polarizers are required, e.g., as is the case in the embodiment of FIGS. 13 and 14 described below.

Figure 12C:
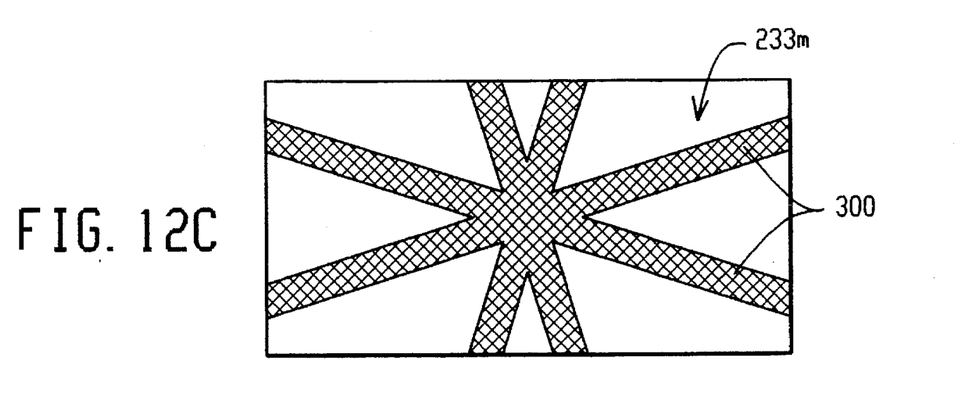
FIG. 12C is a schematic illustration showing superimposed relation of the fields of view of FIGS. 12A and 12B.

Superimposing optically the two optical systems resulting in the fields of view 212, 212B in the manner of FIG. 4, for example, causes a pattern of relatively minimal light transmission 233M of FIG. 13C. The pattern 233M includes a substantial horizontally directed area of substantially uniformly relatively minimal light transmission (dark area 300). Since the large dark area 300 is in approximately the horizontal direction, e.g., relative to the illustration of the drawing and, thus, for example, in the field of view of the eyes of a person wearing a shutter including the optical systems forming fields of view 212, 212B, a relatively wide dark field of view or angle of view is provided the person for maximum eye protection for laterally located sources of light, such as an adjacent welding tool.

By altering the polar direction of the respective polarizers and/or pairs of polarizers, the areas in the field of view of minimal light transmission can be changed. Thus, the mostly horizontal pattern of maximum darkness of FIG. 12C, which is desirable for welding, can be achieved by one relative alignment; and a "star" or more overall uniform pattern such as that depicted in FIG. 5, which is desirable for color display and/or camera applications, also can be achieved. The precise pattern 33, 233, 233M, etc., can be tuned to ensure maximum effectiveness (e.g., darkness or minimal light transmission) in any given application.

Figure 13:
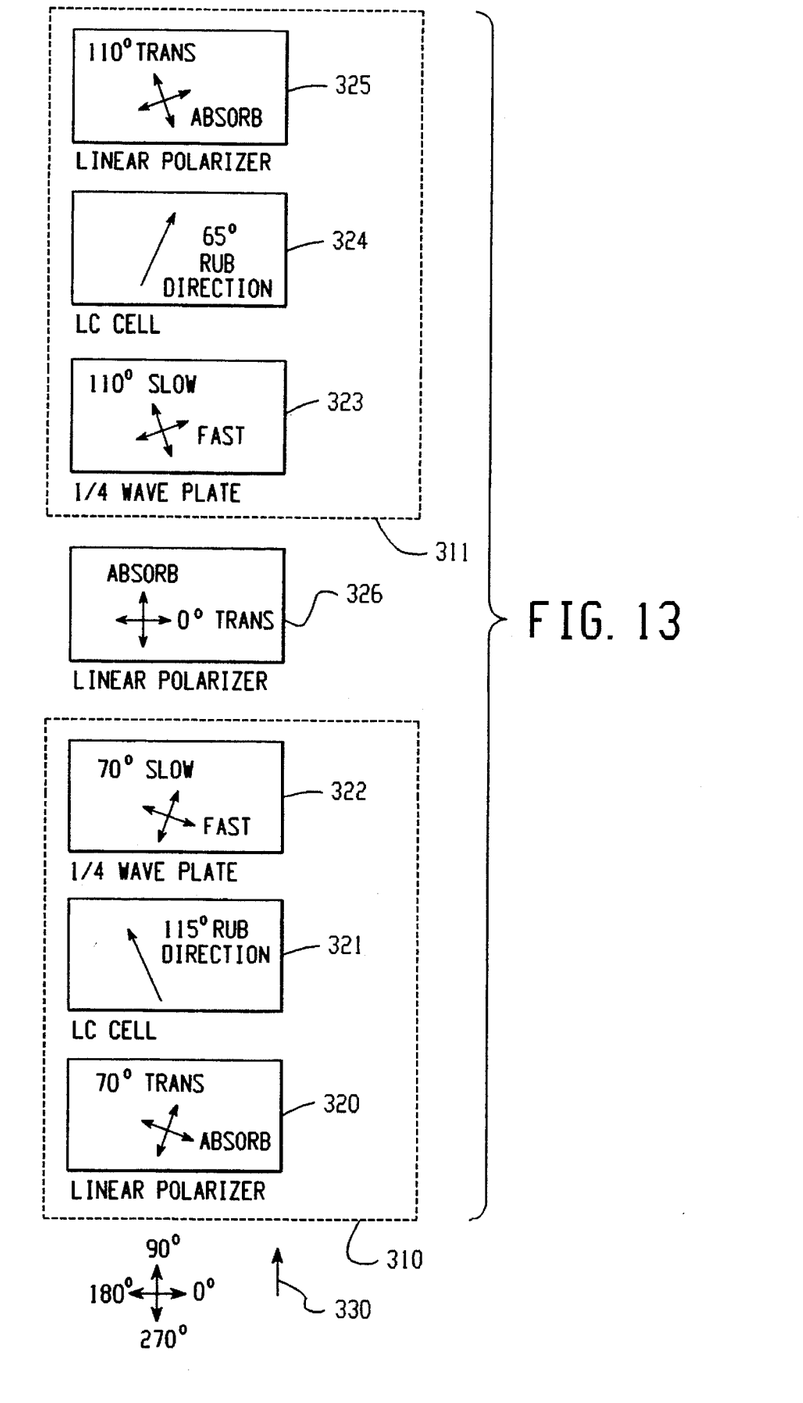
FIG. 13 is a schematic illustration of a light control device including two switchable polarizing components and an analyzer therebetween.
Figure 14:
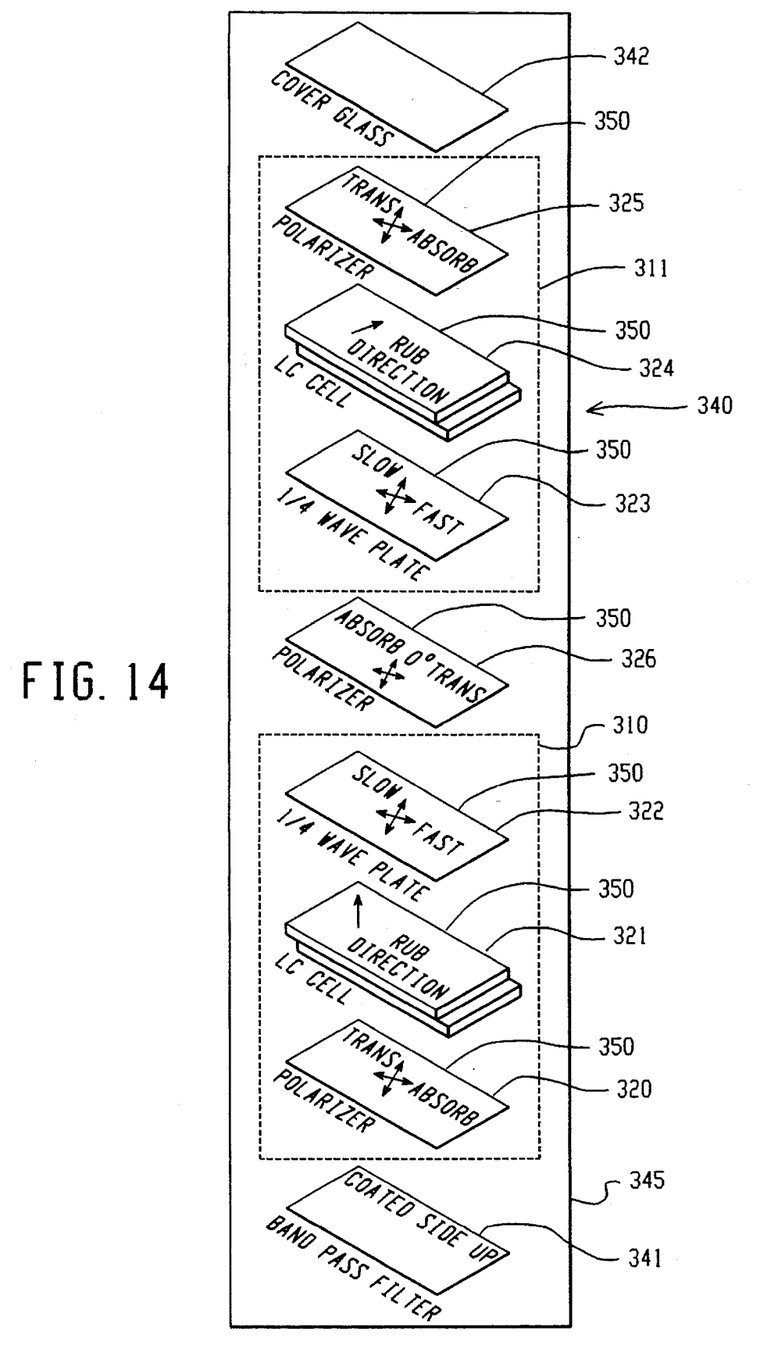
FIG. 14 is a schematic illustration of a light control apparatus including the light control device of FIG. 13 together with additional parts to form, for example, an eye protection device.

Turning to FIGS. 13 and 14, an embodiment of the invention is shown in which duplicate parts are used. Specifically, there are first and second optical components 310, 311 which are optically in series to affect light transmitted therethrough and/or to control, e.g., to block, to permit, and/or to vary, light transmission. The optical components 310, 311 are identical, including the alignment of the components thereof. The difference between the optical components 3 10, 311 is the order with respect to which they are arranged relative to the light propagation direction. For example, light propagates through a polarizer 320, liquid crystal cell 321 and quarter wave plate (or other device for adjusting the quadrature components of light transmitted therethrough) 322 of the first optical component 310 and through a quarter wave plate 323 (or other device for adjusting the quadrature components of light transmitted therethrough), liquid crystal cell 324 and polarizer 325 of the second optical component 311. Another linear polarizer 326, which sometimes is referred to as an analyzer, is located between the two optical components 310, 311 and in effect is shared by both optical components. The liquid crystal cells 321,324 are variable optical retardation or birefringent cells, e.g., surface mode cells; each of which has an alignment direction often referred to as a rub direction, regardless of whether rubbing, evaporation, or some other technique is used to obtain a particular liquid crystal alignment.

In FIG. 13 a vertical arrow 330 represents a reference direction. The transmissive axis of the polarizer 320 is oriented tilted clockwise relative to the reference direction; the transmissive axis of polarizer 325 is oriented tilted counterclockwise an equal amount relative to the reference direction. The rub (or other alignment technique) direction of the liquid crystal cell 321 is oriented tilted counterclockwise relative to the reference direction; and the rub direction of the other liquid crystal cell 324 is oriented tilted clockwise an equal amount relative to the reference direction. The quarter wave plates 322,323 each have fast and slow axes; the respective slow axes are tilted relative to the reference direction the same amounts in the opposite directions. The respective fast axes also are tilted relative to the reference direction the same amounts in the opposite directions.

From the foregoing, then, it will be appreciated that the optical components 310, 311 can be identical. The only difference is that one is "flipped" over relative to the other so that the alignment of the respective relevant transmissive, rub, slow/fast axes directions will be the same amount but reversed relative to the reference direction. Therefore, the light incident side (or first side) of one of the parts, e.g., the liquid crystal cell, of the optical component and the light output side (or second side) of that part, will be reversed for the other optical component.

As an example, the transmissive axes of the linear polarizers 320, 325 may have a polar alignment of plus (in the clockwise direction) and minus 20° (twenty degrees) relative to the reference direction; the polar alignment of the rub directions of the liquid crystal cells 321, 324 may be plus and minus 25° (twenty-five degrees) relative to the reference direction; and the slow axes of the quarter wave plates 322, 323 may have a polar alignment of plus and minus 20° (twenty degrees) relative to the reference direction (the fast axes would be offset by 90° (ninety degrees) relative to the respective slow axes). The effective alignment of the transmissive axes of the two polarizers 320, 325 should be different in the dark state of operation of the optical system in which the optical components 310, 311 are included.

The transmissive axis of the analyzer 326 is oriented orthogonal (or at some other desired direction for a particular operational function) to the reference direction. Therefore, the blocking axis or nontransmissive axis of the analyzer 326 will be parallel to the reference direction.

As is seen FIG. 14, an optical system 340 includes in optical series the optical components 310, 311, analyzer 326, a band pass filter 341, and a cover glass 342. The band pass filter may provide filtering of incident electromagnetic energy, such as infrared, ultraviolet, and/or one or more wavelengths of visible light, the latter possibly for cooperative operation with the optical components 310, 311, for example, as is disclosed in U.S. Pat. No. 5,208,688. The cover glass 342 and possibly also the band pass filter 341 provide protection for the optical components 310, 311 and also may provide protection for the eye of the user of the optical system.

The optical system 340 may be mounted in a frame 345 for mounting relative to the eyes 18 (FIG. 1) of a person. The frame may be in the form of goggles, a welding helmet, or some other device for use to place the optical system 340 between the eyes of a person and a source of light.

The several parts 321-325 of the respective optical components 310, 311 and the analyzer 326 may be of generally plate-like shape. Preferably each of the parts and the analyzer has at least one wall, such as the top edge 350 shown for each part, which serves as a reference with respect to the polar direction of alignment of the transmissive axis, rub direction, slow or fast axis, etc. of the particular part. By properly aligning the respective reference walls of the several parts 321-325 and analyzer 326, orientation with respect to the reference direction easily can be obtained. Some portion of the respective parts other than the walls 350 also or alternatively may be used to facilitate the described aligning of the parts of the optical system 340.

A method of making the optical system 340, then, includes making one of the optical components, say component 310, 311 by aligning the reference walls 350 of the parts 321, 322, 323 relative to each other with the parts in the indicated order of polarizer, liquid crystal cell and wave plate, optically sequentially.. Adhering those parts together. Similarly making the second optical component, either simultaneously or sequentially. Placing the optical components in optical series relative to each other and relative to the analyzer 326. Flipping one of the optical components so that incident light on the optical system 340 impinges first on the polarizer thereof before impinging on the optically proximate liquid crystal cell and so that the output light leaving the optical system exits through a polarizer after transmission through the optically proximate liquid crystal cell. The band pass filter 341 and cover glass are placed relative to the respective optical components 310, 311. The various described parts are assembled in a frame or other mounting means 345.

The described method of making the optical system 340 facilitates manufacturing using a relatively minimal number of parts. This is due in part to use of identical optical components 310, 311. Facility of manufacturing also is enhanced due to the use of a reference direction and the aligning of parts with respect thereto.

It will be appreciated that the optical system 340 may use only three polarizers compared to the illustrated four polarizers in the optical systems of FIGS. 4, 8, 9 and 10. By reducing the number of polarizers used in the optical system and/or by reducing other parts required in the optical system, an increased brightness of the light transmitted through the optical system in the bright or clear state can be achieved. Also, by reducing the number of parts, manufacturing is facilitated and costs of parts and of manufacturing can be reduced.

Further, although several embodiments have been illustrated and described, such illustrations and descriptions are intended to be exemplary, and it will be appreciated that the scope of the invention is intended to be limited only by the following claims and the equivalents thereof.

Statement of Industrial Application

In view of the foregoing, it will be appreciated that the present invention provides apparatus for protecting the eyes of an individual.

The embodiments of the invention in which an exclusive property or privilege is claimed are, as follows:

1. A light transmission control, comprising:

polarizer means including a first polarizer and an analyzer in optical-series having transmissive axes operationally oriented to cooperatively control light transmission through said polarizer means to provide in at least one field of view a relatively dark area and a relatively less dark area, and further polarizer means including a further polarizer having a transmissive axis operationally oriented at an angle other than parallel to the transmissive axes of said first polarizer and analyzer for cooperating with said polarizer means to darken at least part of said relatively less dark area within said at least one field of view.

2. The control of claim 1, said first polarizer and analyzer having transmissive axes oriented substantially operationally orthogonal to one another.

3. The control of claim 1, said further polarizer means further comprising a further analyzer having a transmissive axis oriented operationally at an angle other than parallel to the transmissive axis of said further polarizer.

4. The control of claim 1, further comprising switching means optically in series with said first polarizer and said analyzer for switching the effective optical relation of the transmissive axes of said polarizer and said analyzer selectively to change light transmission through said polarizer means.

5. The control of claim 4, said switching means comprising a liquid crystal cell.

6. The control of claim 5, said liquid crystal cell comprising a liquid crystal cell that affects light based on the principle of variable optical retardation.

7. The control of claim 4, further comprising further switching means optically in series with said analyzer and said further polarizer for switching the effective optical relation of the transmissive axes of said analyzer and said further polarizer selectively to change light transmission through said further polarizing means.

8. The control of claim 7, said further switching means comprising a liquid crystal cell.

9. The control of claim 8, said liquid crystal cell comprising a liquid crystal cell that affects light based on the principle of variable optical retardation.

10. The control of claim 4, said switching means being operative according to the principle of variable optical retardation, said first polarizer, analyzer and switching means being related such that in respective optically functional modes of said switching means relatively less and relatively more light is transmitted by said analyzer.

11. The control of claim 4, further comprising means for adjusting the quadrature components of light transmitted relative to said switching means.

12. The control of claim 11, said means for adjusting comprising a quarter wave plate.

13. The control of claim 7, said switching means and said further switching means each comprising a respective variable optical retardation liquid crystal cell.

14. The control of claim 7, wherein the polar directions of alignment of the transmissive axis of said polarizer and said further polarizer are substantially equi-angularly spaced and on opposite sides of a reference direction.

15. The control of claim 1, wherein the operative orientations of the transmissive axes of respective polarizer and further polarizer are substantially equi-angularly spaced relative to and on opposite sides of a reference direction.

16. Eye protection gear, comprising the light transmission control of claim 1, and mounting means for mounting said light transmission control for eye protection.

17. The gear of claim 16, said mounting means comprising a shield for protecting at least part of the face of a person.

18. The gear of claim 16, said polarizer means being positioned in said mounting means to be located relative to an eye to provide a primary area of substantially minimum light transmission over a generally linear direction that is near but is not horizontal relative to the eye, and said further polarizer means is positioned relative to said polarizer means and located relative to an eye to provide a primary area of substantially minimum light transmission over a different generally linear direction that is near but is not horizontal relative to the eye.

19. A light transmission control, comprising:

polarizer means including a first polarizer and an analyzer in optical series having transmissive axes operationally oriented to cooperatively control light transmission through said polarizer means to provide in at least one field of view a relatively dark area and a relatively less dark area, and further polarizer means including a further polarizer having a transmissive axis operationally oriented at an angle other than parallel to the transmissive axes of said first polarizer and analyzer for cooperating with said polarizer means to darken at least part of said relatively less dark area within said at least one field of view, said polarizer means and said further polarizer means each comprising switching means optically in series with said first polarizer and said further polarizer, respectively, each switching means including a liquid crystal cell for switching the effective optical relation of the transmissive axes of said polarizer and said analyzer selectively to change light transmission through said polarizer means and wherein the polar directions of rub or other alignment of said respective liquid crystal cells are substantially equi-angularly spaced and on opposite sides of a reference direction.

20. The control of claim 19, wherein the polar directions of alignment of the transmissive axis of said polarizer and said further polarizer are substantially equi-angularly spaced and on opposite sides of said reference direction.

21. The control of claim 20, further comprising means for adjusting the quadrature components of light transmitted relative to said switching means and further means for adjusting the quadrature components of light transmitted relative to said further switching means.

22. The control of claim 21, said means for adjusting and said further means for adjusting comprising a respective quarter wave plate.

23. The control of claim 21, wherein said means for adjusting and further means for adjusting have respective slow and fast axes, and wherein the polar alignment directions of the respective slow and fast axes of said means for adjusting relative to the respective slow and fast axes of said further means for adjusting are substantially equi-angularly spaced and on opposite sides of said reference direction.

24. The control of claim 23, wherein said polarizer, further polarizer and analyzer collectively consist of a total of three optical polarizers.

25. The control of claim 20, wherein the direction of the transmissive axis of said analyzer is orthogonal to the reference direction.

26. Eye protection gear, comprising:

a light transmission control, and mounting means for mounting said light transmission control proximate the eyes of a wearer, said light transmission control comprising:

polarizer means for controlling light transmission, including a polarizer and an analyzer operatively related and positioned relative to each other to control transmission of light therethrough, the light transmission appearing in a field of view relative to said polarizer means as having relatively more transmissive and less transmissive areas; and further polarizer means cooperative with said polarizer means for increasing the total amount of area in the field of view having relatively dark light transmission characteristic for light incident from a generally oblique horizontal direction.

27. The eye protection gear of claim 26, said further polarizer means comprising a further polarizer operatively related at an angle other than parallel to the transmissive axes of said polarizer and said analyzer 28. The eye protection gear of claim 27, said further polarizer and said polarizer being operatively related and positioned relative to each other such that the respective transmissive axes thereof are at other than orthogonal relation.

29. The eye protection gear of claim 26, further comprising switching means optically in series with said polarizer and said analyzer for switching the effective optical relation of the transmissive axes of said polarizer and said analyzer selectively to change light transmission through said polarizer means.

30. The eye protection gear of claim 29, further comprising further switching means optically in series with said analyzer and said further polarizer means for switching the effective optical relation of the transmissive axes of said analyzer and said further polarizer means selectively to change light transmission through said further polarizer means.

31. The eye protection gear of claim 30, said switching means and further switching means each comprising a respective liquid crystal cell.

32. The eye protection gear of claim 31, each of said liquid crystal cells comprising a liquid crystal cell that affects light based on the principle of variable optical retardation.

33. A light control device, comprising plural light polarizers, and switching means positioned relative to said light polarizers for switching the relative operational orientation of the respective transmissive axes of at least two of said polarizers. and said light polarizers consisting of only three plane polarizers and said switching means comprising a first liquid crystal cell optically between two of said polarizers and a second liquid crystal cell optically between two of said polarizers, wherein the polar directions of rub or other alignment of said respective liquid crystal cells are substantially equi-angularly spaced and on opposite sides of a reference direction, and wherein the polar directions of alignment of the transmissive axis of two of said polarizers are substantially equi-angularly spaced and on opposite sides of said reference direction.

34. The control of claim 33, further comprising means for adjusting the quadrature components of light transmitted relative to said first liquid crystal cell and further means for adjusting the quadrature components of light transmitted relative to said second liquid crystal cell.

35. The control of claim 34, wherein said means for adjusting and further means for adjusting have respective slow and fast axes, and wherein the polar alignment directions of the respective slow and fast axes of said means for adjusting relative to the respective slow and fast axes of said further means for adjusting are substantially equi-angularly spaced and on opposite sides of said reference direction.

36. The control of claim 33, wherein the direction of the transmissive axis of the third polarizer analyzer is orthogonal to the reference direction and said third polarizer is optically between said first and second polarizers.

37. A light transmission controlling device, comprising three optical polarizers in optical series, each polarizer having a first side for receiving incident light and a second side, two of said polarizers being substantially identical having at least one similarly shaped physical wall (edge) and a transmissive axis oriented in the same direction relative to said physical wall, selectively operable switching means for changing the plane of polarization of light received from one of said polarizers and directing such light to another of said polarizers, and said two of said polarizers being relatively positioned with said physical walls thereof aligned in parallel overlying relation and said second surface of one polarizer facing said first surface of another polarizer whereby the direction of the transmissive axis of one polarizer is different from the direction of the transmissive axis of the other polarizer, said switching means comprising two substantially identical variable optical retardation liquid crystal cells, each having a first side for receiving incident light and a second side, each having a physical wall (edge) aligned in parallel with the other and a rub alignment direction that is substantially the same relative to said physical wall thereof, said two liquid crystal cells being relatively positioned with said physical walls thereof aligned in parallel overlying relation and said second surface of one liquid crystal cell facing said first surface of the other liquid crystal cell whereby the rub alignment direction of one liquid crystal cell is different from the rub alignment direction of the other liquid crystal cell.

38. A method of manufacturing a light transmission control device, comprising assembling a plurality of identical optical components, each having substantially identical alignment characteristics, positioning at least two of said optical components in back-to-back optical series, whereby the polar alignment of at least one part of both of said optical components is equi-angular and opposite sense relative to a reference direction.

39. A light transmission control device, comprising a plurality of identical optical components, each having substantially identical alignment characteristics, at least two of said optical components being positioned in back-to-back optical series, whereby the polar alignment of at least one part of both of said optical components is equi-angularly spaced relative to and on opposite sides of a reference direction.

40. An eye protection device for reducing the transmission of obliquely incident light to the eyes of a user, comprising a first polarizer and a first analyzer in optical series having transmissive axes oriented substantially operationally orthogonal to one another;

a second polarizer and a second analyzer in optical series having transmissive axes oriented substantially operationally orthogonal to one another; said second polarizer and said first analyzer being in optical series and having their transmissive axes oriented relative to one another to reduce leakage of obliquely incident light; and means for positioning said first and second polarizers and said first and second analyzers in proximity to the eyes of a viewer.

41. An eye protection device positionable in proximity to the eyes of a viewer for reducing transmission leakage of light obliquely incident to the eyes of a user, comprising a first polarizer and a first analyzer in optical series having transmissive axes oriented substantially operationally orthogonal to one another;

a second polarizer in optical series with said first polarizer and said first analyzer and having a transmissive axis operationally oriented at an angle other than parallel to the transmissive axes of said first polarizer and said first analyzer for cooperatively reducing leakage of obliquely incident light; and means for positioning said first and second polarizers and said first analyzer in proximity to the eyes of a viewer.

42. The eye protection device of claim 41, further including a second analyzer in optical series with said second polarizer.

43. The eye protection device of claim 42, wherein said second polarizer and said second analyzer have transmissive axes oriented substantially operationally orthogonal to one another.

44. The eye protection device of claim 41, wherein the respective transmission axes of said second polarizer and said first analyzer are oriented substantially at 45 degrees to one another.

45. The eye protection device of claim 41, further including at least one wave plate positioned between said first analyzer and said second polarizer.

46. The eye protection device of claim 41, including a liquid crystal device positioned between said first polarizer and said first analyzer.

47. The eye protection device of claim 46, wherein said liquid crystal device is a tunable birefringence device.

48. The eye protection device of claim 47, wherein said tunable birefringence device is a surface mode liquid crystal device.

* * * * *